US009913991B2

(12) United States Patent
Greiner et al.

(10) Patent No.: US 9,913,991 B2
(45) Date of Patent: Mar. 13, 2018

(54) DEFIBRILLATION APPARATUS FOR WIRELESS DATA EXCHANGE WITH A PATIENT MONITORING APPARATUS

(71) Applicant: KONINKLIJKE PHILIPS N.V., Eindhoven (NL)

(72) Inventors: Harald Greiner, Nufringen (DE); Norman Maurice DeLisle, Manchester, MA (US); Christian Michael Epping, Goeppingen (DE); Marc Cordaro, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/650,679

(22) PCT Filed: Dec. 16, 2013

(86) PCT No.: PCT/IB2013/060986
§ 371 (c)(1),
(2) Date: Jun. 9, 2015

(87) PCT Pub. No.: WO2014/097117
PCT Pub. Date: Jun. 26, 2014

(65) Prior Publication Data
US 2015/0306409 A1 Oct. 29, 2015

Related U.S. Application Data

(60) Provisional application No. 61/738,590, filed on Dec. 18, 2012.

(51) Int. Cl.
*A61N 1/00* (2006.01)
*A61N 1/39* (2006.01)

(52) U.S. Cl.
CPC .................. *A61N 1/3925* (2013.01)

(58) Field of Classification Search
USPC ......................................... 607/5, 7
See application file for complete search history.

(56) References Cited

U.S. PATENT DOCUMENTS 6,405,083 B1 6/2002 Rockwell et al.
6,597,948 B1 7/2003 Rockwell et al.
(Continued)

FOREIGN PATENT DOCUMENTS

WO 2004024232 A1 3/2004

*Primary Examiner* — Nicole F Johnson

(57) ABSTRACT

A defibrillator with wireless communications with a patient monitor. The wireless communications transmits patient data collected by measurement modules between the defibrillator and the patient monitor using wireless nodes when a patient is under cardiac arrest. The transmitted data is integrated with the data already residing on each respective device using data integration modules, and then displayed to the code team in the patient's room on displays, thereby allowing every member of the code team to see data from both devices by reading just one of the displays. The integrated data is also associated with synchronized clocks between the two devices. The integrated data is then compiled into a single unified report comprising the data from both devices and attached to the patient's electronic health record located on a patient record database.

20 Claims, 5 Drawing Sheets

(56) References Cited

U.S. PATENT DOCUMENTS

| | | |
|---|---|---|
| 7,957,798 B2 | 6/2011 | Pearce et al. |
| 2004/0204743 A1* | 10/2004 | McGrath .................. A61N 1/08 |
| | | 607/5 |
| 2007/0032830 A1 | 2/2007 | Bowers |
| 2007/0270909 A1 | 11/2007 | Saketkhou |
| 2008/0058884 A1 | 3/2008 | Matos |
| 2008/0077185 A1* | 3/2008 | Pearce ..................... A61N 1/39 |
| | | 607/5 |
| 2008/0177341 A1 | 7/2008 | Bowers |
| 2009/0131997 A1 | 5/2009 | Cohen et al. |
| 2011/0172550 A1 | 7/2011 | Martin et al. |
| 2012/0123490 A1 | 5/2012 | Daynes et al. |

* cited by examiner

DEFIBRILLATION APPARATUS FOR WIRELESS DATA EXCHANGE WITH A PATIENT MONITORING APPARATUS

CROSS REFERENCE TO RELATED APPLICATIONS

This application is a national filing of PCT application Serial No. PCT/IB2013/060986, filed Dec. 16, 2013, published as WO 2014/097117 A2 on Jun. 26, 2014, which claims the benefit of U.S. provisional application Ser. No. 61/738,590 filed Dec. 18, 2012, which is incorporated herein by reference.

The present application relates to the medical arts and finds particular application with defibrillators and will be described with particular reference thereto. However, it is to be appreciated that it will also find application in other medical interventions and treatment procedures. When a hospital patient becomes unresponsive due to tachycardia or fibrillation, a code team is summoned to the patient's room to attempt resuscitation. The code team typically includes: a physician trained in Advanced Cardiac Life Support, a person who operates a defibrillator from a movable crash cart, one or two people to perform CPR, a medication nurse, a transcription nurse, and other specialists such as a respiratory therapist.

The defibrillator provides a display screen that shows the patient's ECG and other vital signs needed to make a diagnosis. It also shows data related to delivering electrical therapy including shocks and pacing pulses. However, it can be difficult for all code team members to see the defibrillator's display because some are too far away or because the defibrillator is angled away from their sight line.

Frequently, especially in critical care and emergency rooms, there is a large patient monitor mounted near the head of the patient's bed. It is positioned so that it can be easily seen from a wide range of locations while treating the patient.

External defibrillators are medical devices used to treat certain types of cardiac conditions including sudden cardiac arrest due to ventricular fibrillation. The defibrillator delivers an electrical shock to restore the patient's cardiac rhythm. Defibrillators also have capabilities to deliver shocks synchronized with the patient's cardiac rhythm for treating conditions such as atrial fibrillation. In addition, defibrillators have the capability to deliver lower energy electrical pulses for transcutaneous pacing for treating arrhythmias such as bradycardia and tachycardia.

Some defibrillators include patient vital signs monitoring capabilities in addition to the capabilities outlined above for delivering electrical therapies. Typical vital signs measurements incorporated into a defibrillator include ECG, SpO2, non-invasive blood pressure (NBP) and end-tidal CO2. These vital signs measurements provide the diagnostic information needed by the code team responding to an emergency when a patient is unresponsive.

After sudden cardiac arrest, the chances of survival drop by approximately 10% every minute. Therefore it is critical for the code team members to be able to work quickly and efficiently. The code team needs to quickly assess the patient's condition and deliver therapy, as warranted. Assessing the patient's condition typically includes acquiring vital signs data such as an electro-cardiogram (ECG), to view the rhythmic electrical signals that control the heart. If the patient is already connected to a patient monitoring device, the ECG waves might already be displayed on the patient monitor. However, ECG electrodes of the defibrillator are typically also applied to the patient and lead wires must be connected to the defibrillator.

Most critical care areas within a hospital are equipped with dedicated patient monitoring devices. These devices monitor some of the same types of vital signs as a defibrillator and more. Patient monitors can retrieve patient data such as blood pressure, pulse oximetry, pulse rate, and other physiological data from the patient. Further, patient monitors can have vital patient data such as age, race, medical or treatment history that is retrieved from a patient's electronic health record. A patient's electronic health record is a medical record generally located on a hospital database that can be accessed by the patient monitor. The record typically contains patient information such as medical history, age, race, address, and etc.

Typically the display screen of the patient monitor is much larger than the defibrillator. Common defibrillator display sizes range from 16 cm to 21 cm for devices such as Philips XL+™ and MRx™. Patient monitoring devices are available with larger display screens from 37 cm to 58 cm or larger for devices such as on the Philips IntelliVue MP80™ and MX800™.

When a code team assembles in a patient's room when a patient is in advanced cardiac arrest, it is important for the entire code team to have the same information at the same time. With the small defibrillator screen and poor sight lines, not all members can see the defibrillator screen to read vital information necessary to treat the patient. Critical time is also lost moving cables, sensors and electrodes from the patient monitoring device to the defibrillator so that critical vital signs data can be displayed and analysed by the defibrillator. Last, patient event data acquired by defibrillator cannot be easily integrated with data acquired by the patient monitoring device. The defibrillator typically generates its own report that is sent to a defibrillator records center and linked to an electronic patient records system, if available.

In accordance with one preferred embodiment of the present application, a defibrillation apparatus comprises a measurement module; a therapy delivery module; a display module; a transmission node; and a data integration module. The measurement module receives input data from a patient. The therapy delivery module delivers therapy to the patient. The display module displays data to a user. The node transmits data, e.g., over a wireless connection. The data integration module shares data with an exterior patient monitoring apparatus using the wireless node.

In accordance with another preferred embodiment, data transmission is conducted or a wired or serial connection instead of a wireless connection through a wireless node. The wired connection can be Ethernet, USB or the like.

In accordance with another preferred embodiment of the present application, a patient monitoring apparatus comprises a measurement module; a display module; a wireless node; and a data integration module. The measurement module receives input data from a patient. The display module displays data to a user. The wireless node transmits data over a wireless connection. The data integration module shares data with an exterior defibrillation apparatus using the wireless node.

In accordance with a preferred method of the present application, a method for integrating data on a defibrillator comprises the step of receiving input data from a patient using a data integration module within the defibrillator. The defibrillator comprises a measurement module; a therapy delivery module; a display module; a wireless node; and a data integration module. The measurement module receives input data from a patient. The therapy delivery module delivers therapy to the patient. The display module displays data to a user. The wireless node transmits data over a wireless connection. The method further comprises the step of exchanging data with a patient monitor using a data integration module through the wireless connection using the wireless node.

An advantage of the present application is that an entire treatment team can view vital patient data whether on the defibrillator or patient monitor. This allows every team member to provide treatment using the same patient data and avoid communication breakdowns during treatment where the patient's chances of survival lessen with each passing second. The present application further allows creation and storage of complete detailed reports about the treatment using data from both the defibrillator and the patient monitor, which will aid in future treatment of the patient.

Further details, features, and advantages of the present application are disclosed in the following description of exemplary and preferred embodiments of invention with reference to the drawings in which shows:

The present application provides functionality to transmit defibrillator data wirelessly to the patient monitoring device and display it on the patient monitoring device's large display screen. The application also provides functionality to transmit data acquired by the patient monitoring device wirelessly to the defibrillator device so it can be analyzed and displayed by the defibrillator. It further provides functionality to transmit defibrillator event data wirelessly to the patient monitoring device so it can be integrated and recorded with patient data acquired by the patient monitoring device to form a complete medical record in a patient's electronic health record. It also includes clock synchronization so that events and data from both devices can be chronologically merged and recorded in the electronic health record.

Figure 1:
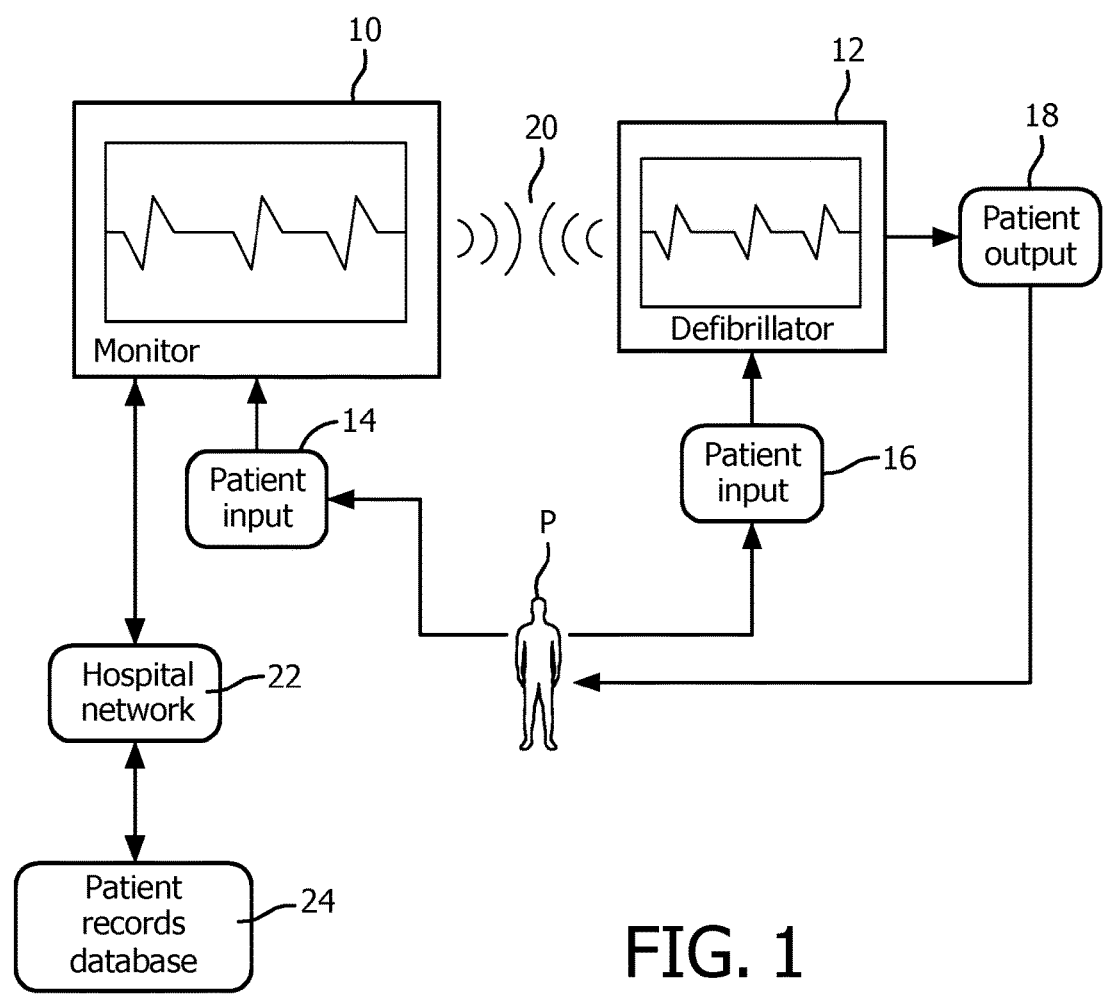
FIG. 1 is diagrammatic of a top level view of an exemplary embodiment of a defibrillator which wirelessly exchanges data with a patient monitor.

FIG. 1 depicts a top-level exemplary embodiment of the system, including a patient monitor 10 and a defibrillator 12 with each receiving input 14, 16 separately from a patient P, a defibrillator output 18 to the patient P, and a wireless connection 20 between the defibrillator 12 and the patient monitor 10. The patient monitor 10 is further connected to a hospital communications network 22, which is connected to a patient record database 24.

The patient monitor 10 is connected to receive vital measurements from the patient. The patient monitor 10, as depicted, displays data via a screen on the patient monitor 10. The patient monitor 10 receives input data, e.g. monitored physiological signals, about a patient from the input 14. The patient monitor 10 further sends and receives data through a wireless connection 20 with the defibrillator 12. The patient monitor 10 forwards the monitored physiological and other data via a healthcare facility network 22 to a patient records database 24 and receives patient information via the network 22 from the patient records database 24 and other input stations, such as lab result input stations, medical emergency stations, and the like.

Further, the patient monitor 10 has a clock that synchronizes with other devices such as the defibrillator 12, in order to ensure that measurements and events from both devices can be integrated and recorded in chronological order in a patient's electronic health record. Any clock synchronization protocol may be used such as PTP, NTP and the like.

The defibrillator 12 is connected to sensors associated with the patient P to receive vital measurements from the patient and provide output therapy to the patient. The defibrillator 12, as depicted, displays data to the user via a screen on the defibrillator device 12. The defibrillator 12 receives input data about a patient from the input 16. The defibrillator 12 further sends and receives data through the wireless connection 20. The defibrillator 12 also has an output 18 to the patient for delivery of therapy from the defibrillator 12. Such therapy, as described above, is applied in instances of advanced cardiac arrest of the patient.

The defibrillator device 12 is representative of a defibrillation device such as the Philips XL+™ and MRx™. Though not shown, the defibrillator device may include a power source, battery pack, ac power input, printer output, hard wired controls or switches for user input, indication lights, or audible alarm module.

The wireless connection 20 can use any wireless connection standard to connect the defibrillator 12 to the patient monitor 10. Once the wireless connection 20 is established between the defibrillator 12 and patient monitor 10, the two devices exchange input data received from the patient at 14 and 16 as well as other data such as patient information and pulses delivered using the wireless connection 20. The exchanged data can be integrated with the data already residing on each respective device and users can read the data on each device's display.

Further, the defibrillator 12 has a clock that synchronizes with other devices such as the patient monitoring device 10, in order to ensure that measurements and events from both devices can be integrated in chronological order to account for any transmission delay and for recordation in a patient's electronic health record. Any clock synchronization protocol may be used such as PTP, NTP and the like.

Figure 2:
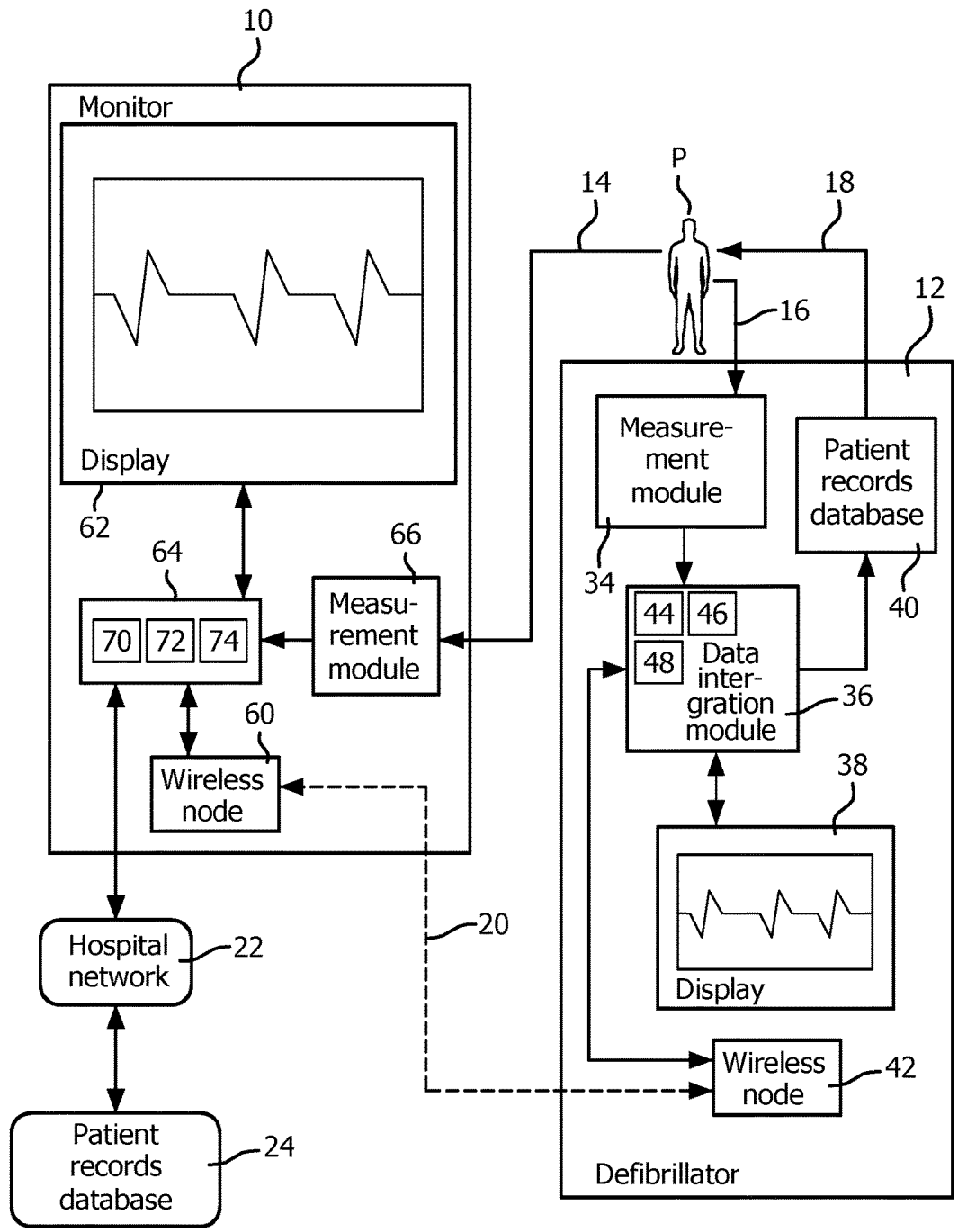
FIG. 2 is a more detailed diagrammatic of the defibrillator and the patient monitor.

With reference to FIG. 2, the defibrillator device 12 includes a defibrillator measurement module 34, data integration module 36, defibrillator display module 38, therapy delivery module 40, and wireless node 42. The defibrillator measurement module 34 is connected at one point to the patient P and another point to the data integration module 36. The defibrillator display module 38 is connected to and controlled by the data integration module 36. The therapy delivery module 40 is connected to the data integration module 36 on one end and to the patient 30 at the other end. The wireless node 42 is connected to the data integration module 36 and supports both wired and wireless networking. The data integration module 36 includes a processor 44, a non-transitory computer readable medium 46 for storage, and a display controller 48 that controls the display 38. In another embodiment, the display controller's 48 function may performed by the processor 44. The processor 44 carries out instructions and functions of the data integration module 36. The non-transitory computer readable medium 46 stores software or firmware that provides instructions to the data integration module 36 as well as provide storage for data within the data integration module 36. The defibrillator device 12 can include different modes of operation including manual mode, a fully automatic mode, a monitoring mode, and a pacer mode.

The defibrillator measurement module 34 is selectively attached to a patient to receive vital measurements and statistics, such as, but not limited to, an electrocardiogram (ECG). The measurement module 34 can be implemented as a combination of software and hardware. The measurement module 34 is connected by leads 16 to the patient P with ECG electrodes and other sensors which pick up physiological data, such as heart rate, ECG patterns, blood pressure, blood oxygen (SpO2) and the like.

The therapy delivery module 40 is attached to the patient P to perform defibrillation techniques at a user's or device's command depending on the defibrillator mode of operation. The therapy delivery module 40 is controlled by the data integration module 36 to apply electric shocks or pulses to the patient in order revive the patient when in advanced cardiac arrest. In one embodiment, the therapy delivery module 40 and the measurement module 34 share a common connection to the patient while performing the respective tasks internally.

Figure 3:
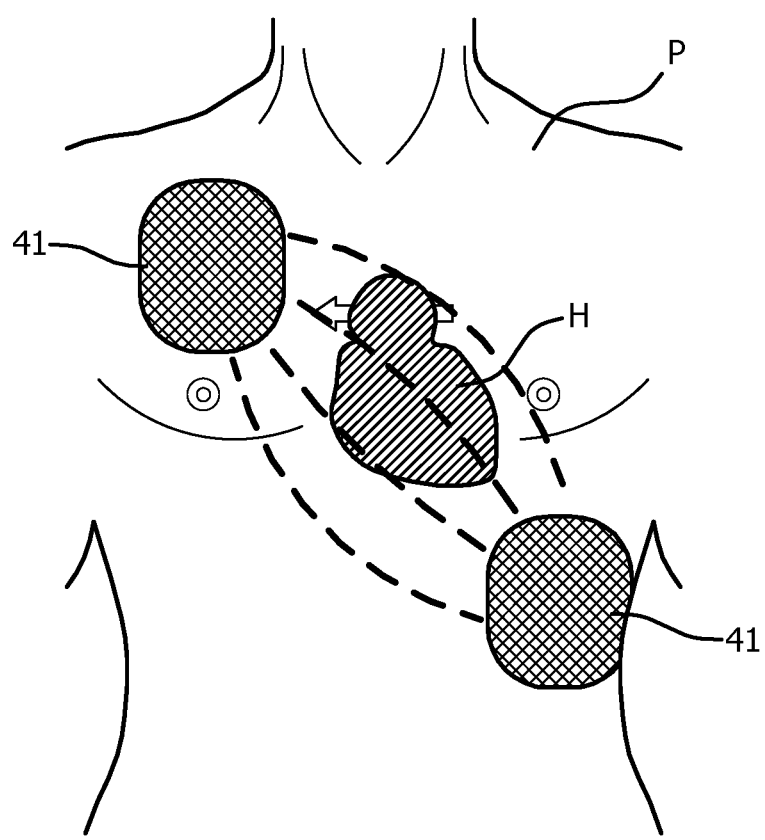
FIG. 3 illustrates defibrillator attachments connected to a patient to deliver therapy and collect patient statistics.

With respect to FIG. 3, the therapy delivery module 40 in one embodiment generates biphasic or monophasic output voltages to the patient. The defibrillation output is transmitted by cables or leads 18 to pads or paddles 41 connected to the patient P such that the biphasic or monophasic voltages are pulsed across the patient's heart H. In another embodiment, the pads 41 are paddles that are applied to the patient to deliver therapy.

In one embodiment, the defibrillator display module 38 is a user interface that includes display monitor and a user input. The user input on the user interface has controls for manipulation of the display and to accept selections by the user. The user can use the user interface to select data to send/receive, choose which data is to be displayed, or send data to the patient's electronic health record from the patient records database 24. The defibrillator display 38 is located on the outside of the defibrillator device to relay information to a user. The user interface displays one or more alarm prompts, user instructions, vital patient information collected from the defibrillator measurement module, and other information useful during the treatment of the patient. Typically, the display module 38 can be an LCD, TFT, LED, CRT or another screen implementation. The user interface includes controls to display the information described above and receive the user inputs. In other embodiments, the user interface controls may include any one of or a combination of a keypad, buttons, knobs, a keyboard, a mouse, a voice recognition system, or the like. In one embodiment, the user interface is controlled by the data integration module 36.

The data integration module 36 is connected to the other modules (the display module 38, the measurement module 34, the therapy delivery module 40, and wireless node 42) located within the defibrillator device 12. The data integration module 36 receives data that is collected by the measurement module 34 and data input from the user interface 38 and sends instructions to the therapy delivery module 40 to apply therapy, and outputs a display signal to the display module 38. The data integration module 36 is connected to a memory 56 which stores vital information about the defibrillator such as current status, therapy applied, alarms, or mode of operation. The data integration module 36 is further connected to the wireless node 42 and makes determinations as to what data is to be shared wirelessly with the patient monitor 10. The data integration module 36 in one embodiment includes a processor which receives data from the measurement module 34, receives data from the wireless node 42, integrates data, sends/receives instructions, presents received data on the display module 38, accepts user inputs through a user interface, and controls the display module 38. Further, the data integration module 36 has a clock that synchronizes with other devices such as the patient monitoring device 10, in order to ensure that measurements and events from both devices can be integrated and recorded in chronological order in the patient's electronic health record. Any clock synchronization protocol may be used such as PTP, NTP and etc.

The wireless node 42 can be any wireless antenna or wireless signal transmitter. The wireless node receives data and instructions to share data with a particular device that is connected to the same patient. The wireless node 42 can detect multiple devices within a desired range and relay the information to the data integration module 36 and the display module 38 which displays a list of patients or monitors from which the user selects the candidate to be connected with the defibrillator 12. Automatic selection can also be used using typical "handshake" protocols. Further, device selection and data transmission can be completed using communication standards like the WPS, Wi-Fi (IEEE 802.11), Bluetooth, IEEE 802.15.4, ZigBee, 6LoWPAN protocols or the like.

The defibrillator wireless node 42 as shown in FIGS. 1 and 2 wirelessly transmits data to a patient monitor wireless node 60 located within the patient monitor device 10. The patient monitor device 10 includes at least a patient monitor display module 62, a data integration module 64, and a patient monitor measurement module 66. The display module 62 can further include a user interface that includes a display and a user input.

The patient monitor measurement module 66 is selectively attached to the patient P to receive vital signs and physiological data, such as but not limited to a blood pressure, pulse rate, pulse oximetry, oxygen levels, hemapathology statistics, and etc.

The patient monitor display 62 is located on the outside of the patient monitor device or on a stand, mounted on a wall or the like, to relay information to a user. In one embodiment, the patient monitor display module 62 is a user interface that includes display monitor and a user input. The user input on the user interface has a touchscreen for manipulation of the display and to accept selections by the user. The user can use the user interface to select data to send/receive, choose which data is to be displayed, or retrieve the patient's electronic health record from a patient records database 24. The display module 62 displays one or more of alarm prompts, user instructions, vital patient information collected from the defibrillator measurement module 34 via the wireless interconnection 20, patient information from the patient's electronic health record, vital signs from the patient measurement module 66 and other information useful during the treatment of advanced cardiac arrest. The display can be an LCD, TFT, LED, CRT and the like. The display can include a touchscreen and other user inputs. In other embodiments, the user interface includes a keyboard, a mouse, a voice recognition system, or the like.

The patient monitor 10 is also connected to a hospital communications network 22 which is connected to the patient record database 24 to get lab reports, patient identification, patient history, age, condition, and the like.

The data integration module 64 is connected to the display module 62, the measurement module 66, and wireless node 60 located within the patient monitor device 10. The data integration module 64 receives data that is collected by the measurement module 66. The data integration module 64 receives data from the patient's electronic health record such as name, age, condition, weight, and the like that is stored on the patient record database 24. The data integration module 64 is further connected to a wireless node 60 to receive physiological data, and defibrillator information and the like. The data integration module 64 also receives via the wireless node 60, control signals from the data integration module 36 regarding what is to be displayed on the patient monitor display module 62. The data integration module 64, based on the available data and the control signals from the defibrillator 12, selects which information is displayed in which order with which selective size. In one embodiment, the data integration module 64 partitions the display, handing over a portion of the display to the data integration module 36. In another embodiment, the data integration module 64 controls the display 62 to copy the display module 38 alone or supplemented by complimentary or redundant physiological data from sensors connected to the patient inputs 14 and 16 as instructed by the data integration module 36 or as specified in a list in a memory 70 through the display controller 72 located within the data integration module 64. In another embodiment, the display controller's 72 function is performed by a processor 74. The data integration module 64 also sends information, such as patient age, sex, condition, physiological data and the like via the wireless node 60 to the wireless node 42 for the data integration module 36 and the therapy delivery module 40 to use in determining parameters of the therapy delivered by the therapy delivery module 40.

The wireless node 60 can be any wireless antenna or wireless signal transmitter. The wireless node receives data and instructions to share data with a particular device that is connected to the same patient. The wireless node 60 can detect multiple devices within a desired range and relay the information to the data integration module and display module. The wireless node 60 can further send unique identifiers in response to a broadcast message, the unique identifiers containing specific identifiers associated with particular patient monitor or the specific candidate patient to be treated. The user can select the desired device to connect with the patient monitor 10. Automatic selection can also be used using typical "handshake" protocols. Further, device selection and data transmission can be completed using communication standards like the WPS, Wi-Fi (IEEE 802.11), Bluetooth, IEEE 802.15.4, ZigBee, 6LoWPAN protocols or the like.

The wireless connection 20 carries uni- or bi-directional wireless transmission between the wireless nodes 42 and 60. In an exemplary embodiment, the wireless data transmission is performed over radio frequency (RF), however, any wireless data transmission standard can perform the data exchange.

The wireless connection 20, in one embodiment, transmits data messages between the two nodes which, as stated above, are then integrated with the data of each home device. Such data messages can be in XML format where the data message transmitted contains a unique identifier as to the type of data being transferred. For example, a message containing noninvasive blood pressure (NBP) values measured by the patient monitor 10 can have the form:

<NBP Measurement> units=mmHg systolic=120 diastolic=80 </NBP Measurement>

The identifier can be easily read by the defibrillator data integration module 36 after reception of the message by the wireless node 42, and can then be displayed on the defibrillator display module 38.

Figure 4:
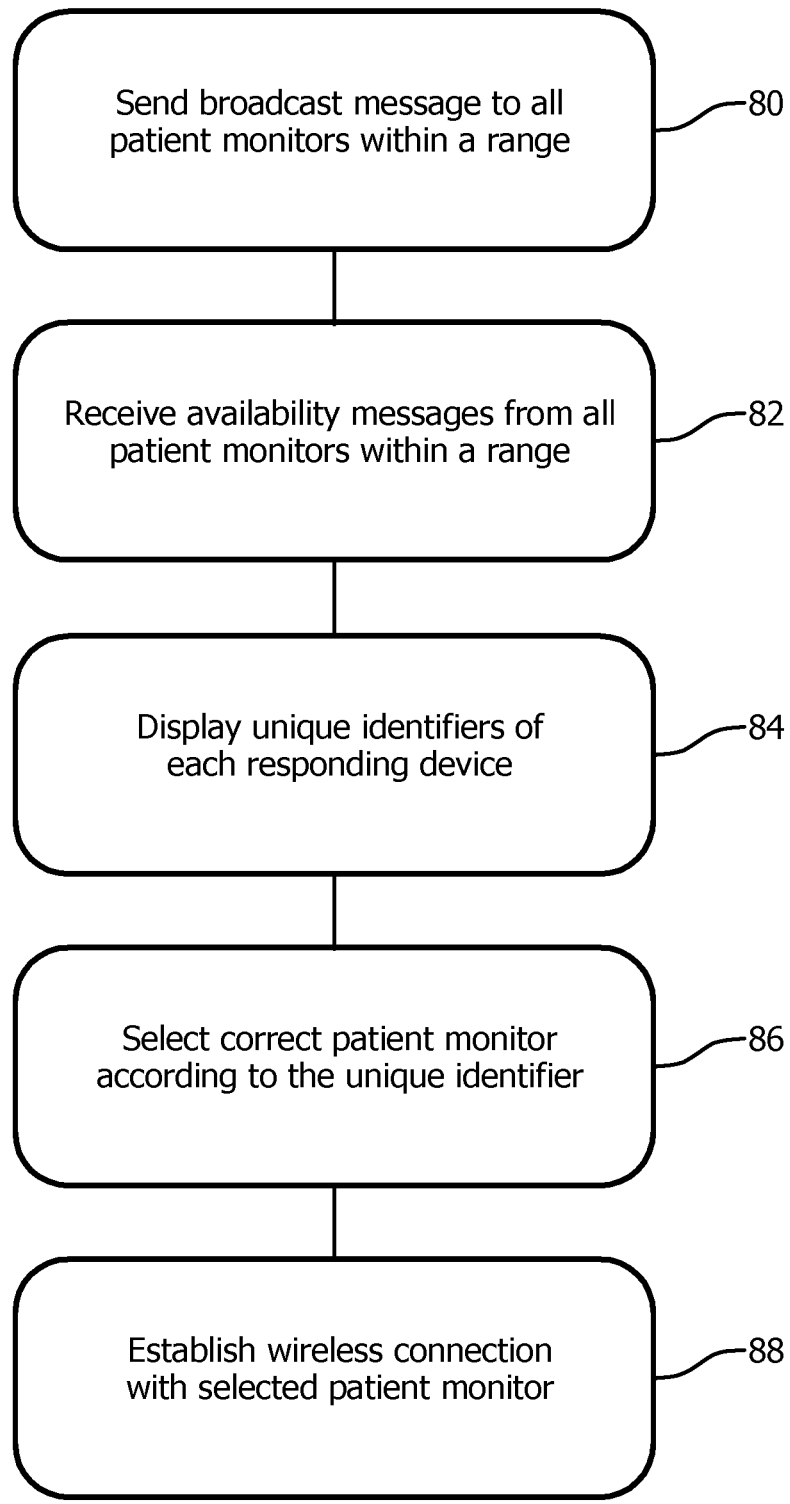
FIG. 4 is a flowchart illustrating an exemplary method of a selection process on the defibrillator device.

With reference to FIG. 4, to connect a patient monitoring device with a defibrillator device, at a Step 80 the data integration module 36 controls the wireless node 42 to broadcast a message to any patient monitors within a range. At a Step 82 the wireless node 42 receives availability messages from all patient monitors within the range. These messages are sent by all patient monitors that receive the broadcast message and have the capability to connect with the defibrillator 12. At a Step 84 the data integration module 36 controls the display module 38 to display the device identifiers of each responding device. At a Step 86 the identifier of the patient to be defibrillated is selected. At a Step 88 a wireless interconnection 20 is established with the selected patient monitor 10. Optionally, the touchscreen monitors of all the responding monitors can display a defibrillator icon which is touched or otherwise selected on the monitor of the patient P to be defibrillated.

Figure 5:
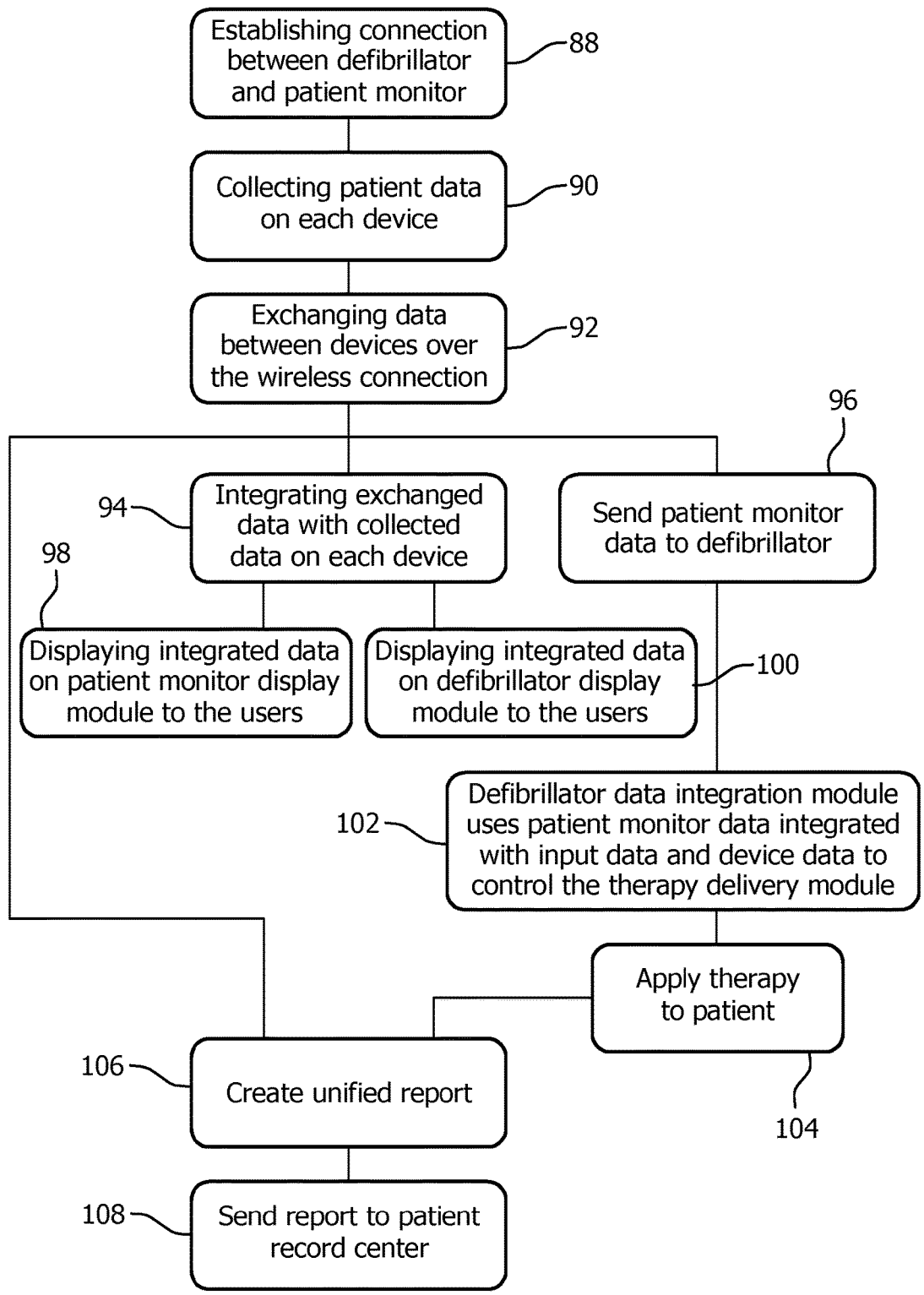
FIG. 5 is a flowchart of an exemplary method for exchanging data between a defibrillator and a patient monitor.

With reference to FIG. 5, at the Step 88, the wireless interconnection 20 is established with the selected patient monitor 10. At a Step 90 patient data is collected by the defibrillator 12 and patient monitor 10 using the measurement modules 34 & 66.

At a Step 92, data is exchanged between devices over the wireless interconnection 20. The exchanging step 92, through the wireless nodes 42 & 60, wirelessly transmits vital sign measurements and information from the patient monitoring device 10 to the defibrillator for integration and display. Therefore, the code team does not lose critical time moving cables between the patient monitor and the defibrillator or swapping electrodes and sensors on the patient.

The data from the defibrillator may log the data from the monitor. Due to the transmission times, a time offset can be included such that the displayed data from the monitor and the defibrillator are synchronized and such that the defibrillator stimulations can be synchronized with the displayed data.

In one embodiment, the defibrillator (12) and patient monitor (10) synchronize time where the defibrillator data integration module's (36) processor (44) requests a time from the patient monitor apparatus (10); receives a time response from the patient monitor apparatus (10); sets the time of the defibrillation (12) according to the time response received such that the defibrillator (12) and the patient monitor apparatus (10) are synchronous; and associates the data collected and received with the synchronized time data.

At a Step 94, the exchanged data is integrated with the collected data on one or both devices. The method and apparatus exchanges the defibrillator data and patient monitoring data. Critical data displayed on the defibrillator screen is wirelessly transmitted to the patient monitor where it can be viewed more readily by members of the code team. Critical data includes vital signs measurements, physiological alarms, therapy delivery events, and user prompt messages.

At a Step 98, the integrated data is displayed on the patient monitor display module 62 to the users. Further, at a Step 100, the integrated data is displayed on the display module 38. The data integration module integrates vital sign measurements acquired by the patient monitor with vital signs measurements acquired by the defibrillator and vice versa. Therefore, the patient monitoring device displays a combination of the data that it acquires from its own sensors with data it receives from the defibrillator. Because of the data integration aspects, the displays on both the defibrillator and the patient monitoring device will be populated with the vital signs measurement data acquired by either device. For example, if the patient monitoring device has an SpO2 sensor applied to the patient, the SpO2 measurement data will be displayed on the patient monitoring display and it will be transmitted wirelessly to the defibrillator for display on the defibrillator display. Similarly, the ECG wave data acquired by defibrillator pads will be displayed on the defibrillator display screen and transmitted wirelessly to the patient monitoring device for display. Hence, there is no need for the code team to move sensors or cables from one device to the other. The displays' organization or layout of information can be the same or unique for the patient monitor and defibrillator.

At a Step 96, patient monitor data is sent to the defibrillator 12, which will be sent to the data integration module 36. This step allows the defibrillator to access complete information from both the defibrillator and the patient monitor. In one embodiment, the data integration module 36 assumes control of all or a portion of the patient monitor display 62, controlling it to display the information most needed to the defibrillation team.

At a Step 102, the data integration module 36 uses the patient monitor data, particularly the age, illness (weakness), sex, whether the patient has in internal pacemaker, and etc., integrated with the data already residing on the defibrillator to control the therapy delivery module 40. With the integrated data, the defibrillator has complete information to make the best therapy related decisions for the patient by way of using the integrated data to directly affect the control of the therapy delivery module 40. In this manner, defibrillation pulses appropriate to the age and condition of the patient P are delivered at the output 18.

At a Step 104, therapy is applied to the patient using the therapy delivery module 40 that is connected to the patient using the leads 18. As discussed above, the therapy deliver module 40 applies therapy in the form of electric shocks across the patient's heart H.

At a Step 106, a unified report is created out of the entire volume of integrated data collected by the patient monitor 10. This report will include the data collected and exchanged and used during treatment of the patient, and provides a singular report that can be accessed and reviewed later.

At a Step 108, the unified report is sent to the patient records center 24 through the hospital communication network 22. The patient monitor 10 alters or adds to the patient's electronic health record for detailed and updated reports after advanced cardiac arrest. The report is then associated with the patient's electronic health record and will help with any further treatment of the patient after cardiac arrest.

In one embodiment, the above described steps are performed by the processors 44 and 74 resident in the monitor 10 and the defibrillator 12 working in concert. In some embodiments, the defibrillator processor 44 will control the process. The memories 46 and 70 are non-transitory computer readable media which carry software for controlling the processors 44 and 74 to perform the above described steps. In another embodiment, the monitor measurement module 66 and data integration module 64 are incorporated in one or more processors. In another embodiment, control of defibrillator measurement module 34, control module 36 and therapy delivery module 40 are incorporated in one or more processors, ASICs, or other combinations of software and/or hardware.

The method, system and apparatus according to the present application are not only applicable to defibrillators and patient monitors, but e.g. as well in other systems or environments which are subject when wirelessly integrating data among multiple devices.

Although the system, apparatus and method of the present disclosure have been described with reference to exemplary embodiments thereof, the present disclosure is not limited to such exemplary embodiments. Rather, the system, apparatus and method disclosed herein are susceptible to a variety of modifications, enhancements and/or variations, without departing from the spirit or scope hereof. Accordingly, the present disclosure embodies and encompasses such modifications, enhancements and/or variations within the scope of the claims appended hereto.

The invention claimed is:

1. A defibrillator, comprising:
   a defibrillator node configured to transmit data over a connection;
   one or more processors programmed to:
   receive input data of a patient collected by using the defibrillator; and
   exchange data with a patient monitor configured to monitor physiological data of the patient using the defibrillator node including:
   establish a wireless connection between the defibrillator and the patient monitor;
   receive the patient data collected by both the defibrillator and the patient monitor;
   exchange data between the defibrillator and the patient monitor over the wireless connection, the exchanged data including information of whether the patient has an internal pacemaker; and
   integrate the exchanged data with collected data; and
   display the integrated data on a display module; and
   a therapy delivery module configured to deliver therapy to the patient based on the integrated data including the information of whether the patient has the internal pacemaker.

2. The defibrillator according to claim 1 in combination with the patient monitor, the patient monitor including:
   a monitor measurement module configured to receive input data from a patient;
   a monitor display module configured to display data to a user(s);
   a monitor wireless node configured to transmit data over a wireless connection; and
   a monitor data integration module configured to exchange data with the defibrillator using the wireless node.

3. The defibrillator and patient monitor combination according to claim 2, wherein the one or more processors are further programmed to display data received from the defibrillator using the monitor display module.

4. The defibrillator and patient monitor combination according to claim 3, wherein the one or more processors are further programmed to:
   using the defibrillator wireless node, send a broadcast message to patient monitors within a range;
   receive availability messages from the patient monitors within range;
   display unique identifiers of each responding patient monitor on a defibrillator display module of the defibrillator;
   receive an operator selection of the patient monitor corresponding to the patient to be defibrillated; and
   establish a wireless connection with the patient monitor.

5. The defibrillator and patient monitor combination according to claim 3, wherein the one or more processors are further programmed to:
   request a time from the patient monitor;
   receive a time response from the patient monitor;
   set the time of the defibrillator according to the time response received such that the defibrillator and the patient monitor are synchronous; and associate the data collected and received with synchronized time data.

6. The defibrillator and patient monitor combination according to claim 3, wherein the one or more processors are further programmed to:
generate a unified report by integrating all data collected and received from the defibrillator and the patient monitor;
transmit the report between the wireless nodes;
send the unified report from the patient monitor to a patient record database using a hospital communications network.

7. A patient monitor apparatus, comprising:
a measurement module configured to receive input data from a patient;
a wireless node configured to transmit data over a wireless connection;
a data integration module configured to exchange data with a defibrillation apparatus using the wireless node including:
  establish a wireless connection between the defibrillation apparatus and the patient monitor apparatus;
  receive patient data collected by both the defibrillator apparatus and the patient monitor apparatus;
  exchange data between the defibrillator apparatus and the patient monitor apparatus over the wireless connection, the exchanged data including an illness of the patient; and
  integrate the exchanged data with collected data on the patient monitor apparatus;
a display module configured to display the integrated data;
a therapy delivery module configured to deliver therapy to the patient based on the illness of the patient;
a receiving module configured to receive a unified report created by the defibrillator apparatus by integrating all data collected by the defibrillator apparatus and patient monitor apparatus; and
a sending module configured to send the unified report from the patient monitor to a patient record database using a hospital communications network.

8. A method of operation for a defibrillator, the method comprising:
receiving input physiological data from a patient with the defibrillator;
wirelessly exchanging data with a patient monitor apparatus including:
  establishing a wireless connection between the defibrillation apparatus and the patient monitor apparatus;
  receiving patient data collected by both the defibrillator and the patient monitor apparatus;
  exchanging data between the defibrillator apparatus and the patient monitor apparatus over the wireless connection, the exchanged data including information of whether the patient has an internal pacemaker; and
  integrating the exchanged data with collected data;
displaying the integrated data on a display module of the defibrillator and/or a display module of the patient monitor apparatus; and
controlling the defibrillator to deliver an electrical shock to the patient based on the integrated data including the information of whether the patient has an internal pacemaker.

9. The method according to claim 8, further including displaying the integrated data on a display module of the patient monitor apparatus.

10. The method according to claim 8, further including displaying the integrated data on a display module of the defibrillator.

11. The method according to claim 8, further including:
sending a broadcast message wirelessly to patient monitors within a range;
receiving reply messages from the patient monitors within range;
displaying unique identifiers of each responding patient monitor;
selecting one of patient monitors which corresponds to the patient to be defibrillated; and
establishing a wireless connection with the one of patient monitors.

12. The method according to claim 8, further including displaying the integrated data on both a display module of the defibrillator and a display module of the patient monitor apparatus.

13. The method according to claim 8, further including:
requesting a time from the patient monitor;
receiving a time response from the patient monitor;
setting a time of the defibrillator according to the time response to synchronize the defibrillator and the patient monitor; and
associating the patient physiological data collected and received with the synchronized time data.

14. The method according to claim 8, further including:
generating a unified report;
sending the unified report from the patient monitor over a hospital communications network to a patient record database.

15. A non-transitory computer readable medium carrying software for controlling one or more processors to perform the method according to claim 8.

16. A defibrillator including a defibrillator processor and a patient monitor including a monitor processor, the defibrillator and patient monitor processors being programmed to perform the method of claim 8.

17. A patient care system including:
a patient monitor including:
  a monitor display configured to display patient physiological data, and
  one or more monitor processors programmed to:
    control the monitor display;
    receive wireless beacon signals from a defibrillator; and
    respond to the received beacon signals by wirelessly sending out an
    identification of the patient monitor; and
a mobile defibrillator including:
  one or more defibrillator processors, programmed to:
    control the defibrillator to transmit the beacon signal;
    receive monitor identifications for one or more patient monitors;
    establish two-way wireless communications with a selected identified monitor;
    receive patient monitor data from the patient monitor including an illness of a patient;
    deliver therapy to the patient based on the illness of the patient; and
    assume control of at least a portion of the monitor display of the patient monitor.

18. The defibrillation apparatus according to claim 1, wherein:

the exchanged data between the defibrillator and the patient monitor apparatus over the wireless connection includes receiving an SpO2 measurement from the patient monitor apparatus; and the display the integrated data on a display module of the patient defibrillation apparatus includes displaying the SpO2 measurement.

19. The defibrillation apparatus according to claim 1, wherein the therapy delivery module is further configured to deliver the therapy to the patient based on an illness of the patient that is included in the exchanged data between the defibrillator and the patient monitor over the wireless connection.

20. The patient care system according to claim 17, wherein:

the patient monitor further includes a wireless node;

the mobile defibrillator further includes a wireless node;

the wireless node of the patient monitor is configured to exchange data messages in an XML format with the wireless node of the mobile defibrillator; and at least one exchanged data message in the XML format includes an identifier identifying the type of data being transferred as noninvasive blood pressure data.

* * * * *